United States Patent [19]
Kikinis

[11] Patent Number: 5,390,673
[45] Date of Patent: Feb. 21, 1995

[54] MAGNETIC RESONANCE IMAGING SYSTEM

[75] Inventor: Dan Kikinis, Saratoga, Calif.

[73] Assignee: Cordata, Incorporated, Tortola, Virgin Islands (Br.)

[21] Appl. No.: 182,745

[22] Filed: Jan. 14, 1994

[51] Int. Cl.$^6$ .............................................. A61B 5/055
[52] U.S. Cl. .............................. 128/653.2; 128/653.5; 324/309; 324/318
[58] Field of Search .......................... 128/653.2, 653.5; 324/307, 309, 318; 600/13-15

[56] References Cited

U.S. PATENT DOCUMENTS

| | | | |
|---|---|---|---|
| 4,672,972 | 6/1987 | Berke | 128/653.5 |
| 4,875,486 | 10/1989 | Rapoport et al. | 128/653.2 |
| 4,985,678 | 1/1991 | Gangarosa et al. | 128/653.2 |
| 5,153,516 | 10/1992 | Gopalsami et al. | 324/309 |
| 5,170,789 | 12/1992 | Narayan et al. | 324/318 X |
| 5,183,045 | 2/1993 | Takamura et al. | 128/653.2 |
| 5,194,809 | 3/1993 | Lew | 324/309 |
| 5,233,300 | 8/1993 | Buess et al. | 324/307 |
| 5,303,707 | 4/1994 | Young | 324/309 X |
| 5,323,778 | 6/1994 | Kandarpa et al. | 128/653.2 |

*Primary Examiner*—Lee S. Cohen
*Assistant Examiner*—Brian L. Casler
*Attorney, Agent, or Firm*—Donald R. Boys

[57] ABSTRACT

A magnetic resonance imaging system has an elongate hand-held probe with a permanent magnet positioned within the probe to align the pole axis of the permanent magnet with the central axis of the probe. A burst/sense electromagnetic coil is positioned to provide a magnetic field coaxial with that of the permanent magnet. The burst/sense coil provides high frequency bursts to excite nuclei in a sample with the end of the probe held proximate a surface of the sample. Bursts are alternated with sensing periods to sense echo from resonating nuclei in the sample. The sensed point in a sample volume can be moved by altering the burst frequency. In another aspect a bias field is provided by the burst/sense coil, and deflection coils are used to move the sensed point through a slice by deflecting the summed permanent and bias field. Different slices are sensed by changing the bias field and repeating sensing an array of points in a new slice. The probe is integrated with a general-purpose computer to provide control, recording of sensed values, assembly of bit maps, and display of images.

17 Claims, 4 Drawing Sheets

5,390,673

MAGNETIC RESONANCE IMAGING SYSTEM

FIELD OF THE INVENTION

The present invention relates generally to medical imaging systems, specifically to a magnetic resonance imaging system having a hand-held probe for imaging small areas of a sample.

BACKGROUND OF THE INVENTION

Magnetic resonance imaging (MRI) is a technique for producing high resolution images of the interiors of samples under study. One application is the imaging of human bodies: MRI machines can produce detailed, cross-sectional images of patients. The images, or slices, can be digitally "stacked" together to form three dimensional views of internal organs and tissue structures. It allows doctors to look inside human bodies without cutting. MRI is one of the most important medical diagnostic tools today.

Most elements have at least one abundant isotope whose nucleus is magnetic. Because such a nucleus is dipolar, it behaves as a very small magnet. When the nucleus is placed in a strong external magnetic field, it will be aligned with the field. A weak but rapidly alternating magnetic field alters the orientation of the nuclei, which causes it to absorb energy. When the nuclei realigns itself with the strong field and returns to equilibrium, it emits energy which can be detected by an antenna placed nearby. This precession is continuously repeated during the application of the alternating magnetic field. The resonance frequency of each nuclear species is determined by its unique precessional properties, and the strength of the magnetic field. This is expressed in the formula $\omega = \gamma H$, where $\omega$ is in radians per second, $\gamma$ is the gyromagnetic ratio characteristic of the nuclear species, and $H$ is the magnetic field. Therefore, all magnetic nuclei of the same species, e.g., hydrogen nuclei in tissue water, will have the same resonance frequency at a particular field strength, regardless of their spatial position in a sample. These principles form the basis of MRI.

A conventional MRI machine includes the following basic components: (1) a ring-shaped enclosure housing a very large magnet capable of producing a very strong, homogeneous magnetic field on the order of 1 to 2 Tesla. A homogeneous field is one in which the field strength is substantially the same at all points within the volume of interest; (2) radio frequency gradient coils for producing weaker, linear gradient fields in each of the three main axes. A linear gradient field is one in which the field strength varies in a linear manner along a particular axis; (3) a sensor coil for detecting emissions as the nuclei precess; and (4) a computer with a display for producing an image bases on the received signals.

An object to be studied, e.g., a human, is placed in the homogeneous or main field within the hole in the enclosure. When a linear gradient field is added, nuclei at different positions within the object will experience different magnetic field strengths, and therefore will precess at different resonance frequencies. The signals given off are detected by the sensor coil as complex wave forms, which are converted to frequency spectra by the computer using Fourier transformation. The resonance frequency of the signal from a nucleus is proportional to the field strength, which in turn is proportional to the distance between the point of interest and the gradient coil. Therefore the position of the nucleus can be determined by imposing gradients in different directions and detecting the frequencies of the signals.

Conventional MRI machines used in medical applications are designed to image entire sections of humans, e.g., to produce images of a brain or part of a torso. The magnets are large enough to surround their subjects, and produce extremely strong fields. Permanent magnets are not suitable for such machines, because when sized for humans, they can weight as much as 113,700 kg (250,000 lb.). Superconducting magnets are generally used because their electrical efficiency allows them to produce extremely strong, homogeneous fields at human-size apertures, and their stability is excellent.

Although conventional MRI machines are powerful tools, they have some disadvantages. Their superconducting magnets are expensive to produce, and they require cryogenic cooling. Their extremely powerful fields attract ferrous objects from many meters away, which can become dangerous projectiles. The large size of the magnets and the ancillary equipment fill whole rooms, so that they are limited to operation at fixed sites. They are also very expensive to operate.

What is needed is a hand-held instrument compatible with a general-purpose computer, capable of imaging small portions of anatomy, such as the human eye, and of producing images of the scanned volume on the display of the general-purpose computer.

SUMMARY OF THE INVENTION

A hand-held probe is provided for magnetic resonance imaging comprising an elongated housing configured to be held and manipulated in a user's hand, with a permanent magnet supported within the housing with one pole facing one end of the housing. The pole axis of the permanent magnet is substantially parallel with the length of the elongated housing. An electromagnetic combination burst and detector coil is positioned to provide a magnetic field coaxial with the magnetic field of the permanent magnet, and electrical conductors are connected to the combination burst and sensor coil for providing high frequency magnetic bursts to excite nuclei in a sample, and to conduct induced signals away from the coil. A cable is provided for conducting power and sensed signals between the probe and a host.

As the field provided by the permanent magnet is not collinear, but gradiated, points within the volume near a pole of the permanent magnet may be distinguished by just changing the burst frequency. In another aspect, a particular point of specific field intensity is sensed and deflected by deflection coils to provide for sensing points in a two-dimensional slice through a sample volume. By adding a bias field with the burst/sense coil, progressive slices through a sample may be scanned for presence of specific nuclei.

To compensate for deterioration of field strength from the permanent magnet, a calibration apparatus is provided incorporating a fixed and known array of sensible elements. An image is stored in the control system for the hand-held probe representing the image provided by a new magnet. An image of the sensible elements taken by a probe with a magnet that has deteriorated may then be compared to the theoretical image to develop a table of corrections to compensate for the deterioration.

The hand-held probe provides a portable, inexpensive, and useful tool for imaging small volumes, such as the human eye, arteries in open heart surgery, and other small surgical fields.

DESCRIPTION OF THE PREFERRED EMBODIMENTS

A small, hand-held MRI probe can be constructed with a very compact but powerful rare earth permanent magnet, such as neodymium-iron-boron (NdFeB). The field strength of such a magnet may exceed 1 Tesla, which is as much as that in conventional machines that use superconducting electromagnets.

Figure 1:
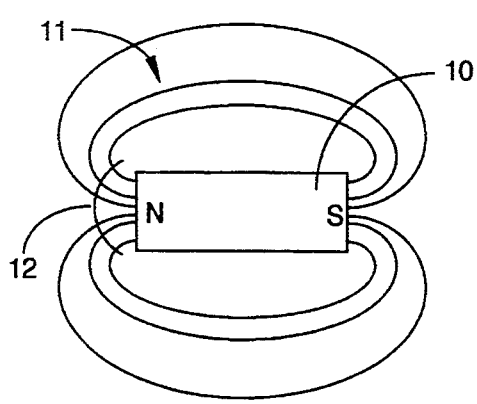
FIG. 1 is an elevation view of a permanent magnet as used in an embodiment of the present invention, showing field lines.

As shown in the side view in FIG. 1, a NdFeB magnet 10 has magnetic field lines 11 extending between its poles. Field lines 11 curve away from each other along all points, so that a field gradient exists. Magnet 10 is rectangular, so that its field shape can be accurately determined. Therefore the field strength at any point near magnet 10 can be accurately calculated after a reference strength is measured at an arbitrary point. Directly in front of either pole, there are points in space that experience the same field strength along a quasi-elliptical surface 12 which is perpendicular to field lines 11 at all points. In three dimensions, surface 12 is an eggshell-like surface (not shown). Surface 12 is shown as an example—similar surfaces of substantially constant field strength may be drawn closer or further from magnet 10.

Figure 2:
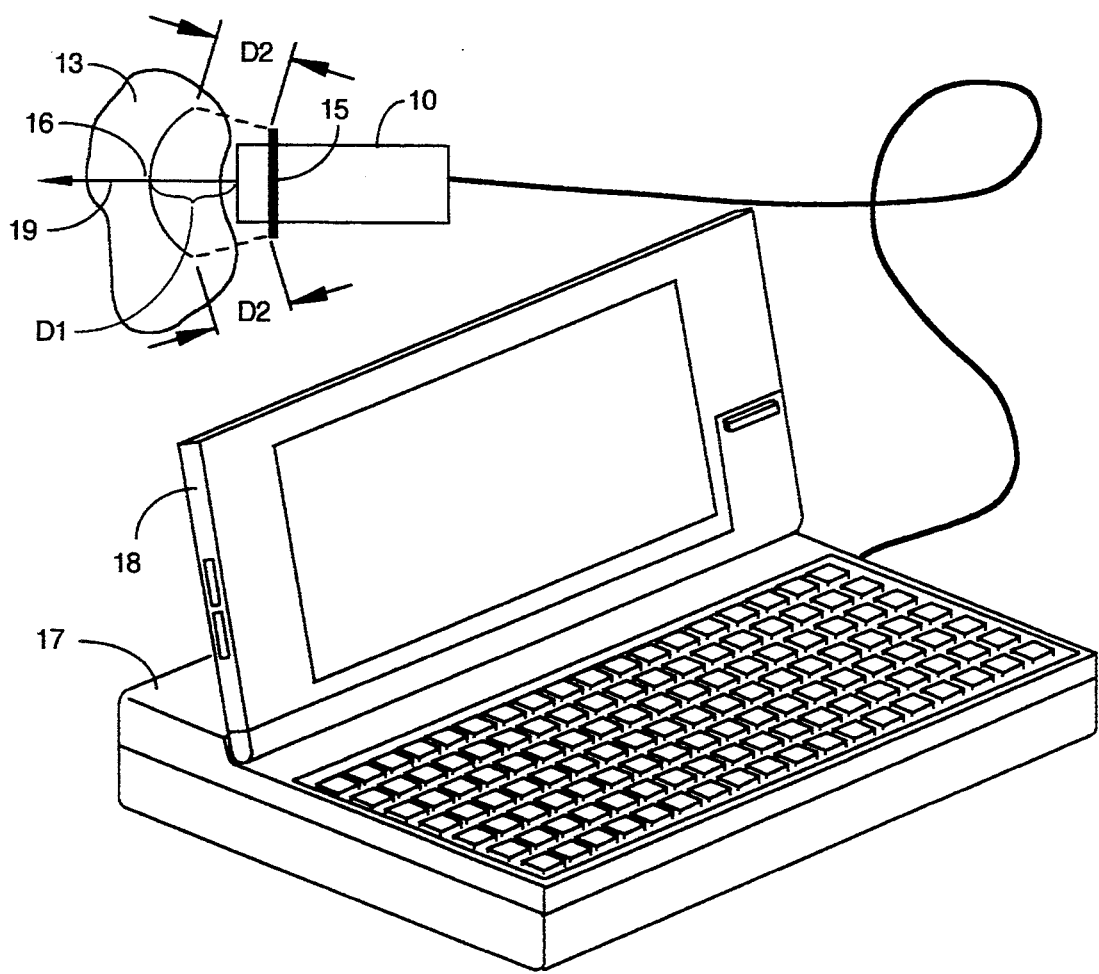
FIG. 2 is a partly diagrammatical view of a hand-held MRI probe in an embodiment of the present invention, connected to a general-purpose computer and held adjacent to a sample to be scanned.

When magnet 10 is placed adjacent a tissue sample 13, as shown in FIG. 2, the hydrogen nuclei in tissue water along surface 12 will be magnetized at a substantially constant field intensity. Therefore these nuclei will have the same resonance frequency, which in the case of hydrogen in water is between about 88 Mhz and 103 Mhz. Because the field strength along surface 12 is known, the resonance frequency of all hydrogen nuclei in surface 12 can be predicted. A combination burst and sensor coil 15 placed around the front of magnet 10 is switchable between the two modes of burst and sense. Coil 15 first emits a burst of magnetic energy at the resonance frequency for the field intensity in surface 12, so that only the nuclei in surface 12 will be excited. Coil 15 is then switched into sensor mode to detect the echoes of the pulse given off by the exited hydrogen nuclei as they return to equilibrium.

Figure 3:
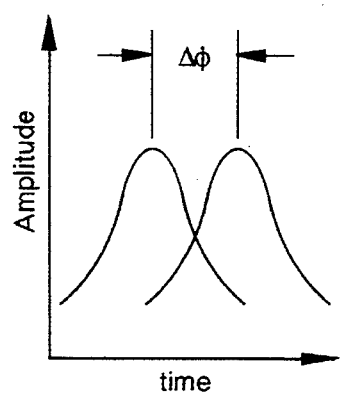
FIG. 3 is a simple graph showing burst-echo phase shift.

The farthest point on surface 12 from coil 15 is imaging point 16. It lies along vector 19 of the magnetic field at a distance D1 from any point on coil 15. The outer edges of surface 12 are at distance D2 from coil 15. When coil 15 sends out a burst at frequency $f_b$, all nuclei in surface 12 respond with an echo. Because point 16 is the farthest from coil 15, the echo produced by a nucleus there will take the longest to reach coil 15, i.e., it will have the greatest phase shift relative to the burst, as shown in FIG. 3. Therefore, an image of point 16 or any other desired point within sample 13 can be produced in the following manner:

1. Determine the field strength at distance D1 or any other desired distance to surface 12;
2. Determine the resonance frequency of a hydrogen nucleus at that field strength;
3. Determine the phase shift of an echo from a nucleus at the point of interest;
4. Send out a burst from coil 15 at the predetermined resonance frequency;
5. Detect the presence or absence of an echo having the predetermined phase shift;
6. Analyze the echo signal, if present, with a notebook computer 17 using conventional algorithms, and display the image on its monitor 18.

The practical resolution of the MRI probe will be limited, i.e., the volume throughout which an imaging point may be established will be a small volume. The volume will be large enough, however to image such as a human eye or a heart artery of interest in open-heart surgery. It will be apparent to one with skill in the art that the relatively small imaging volume with a hand-held probe will have very many other useful applications.

Figure 4A:
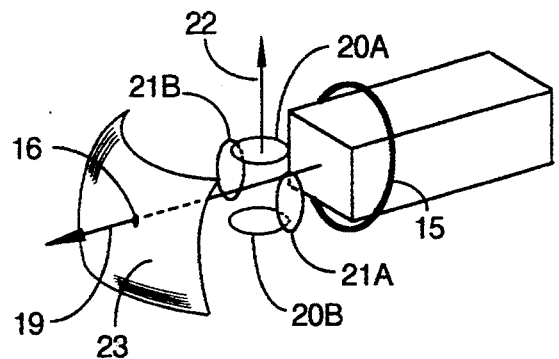
FIG. 4A is an isometric illustration of a permanent magnet and steering coils in an embodiment of the invention.

In an aspect of the invention, the interior of a sample 13 can be probed systematically, one point at a time, to produce two-dimensional as well as three-dimensional images. This is done by steering the field of magnet 10, i.e., the main field, with adjustable steering fields positioned around the front of the magnet. As shown in FIG. 4A, vector 19 of the main field represents the Z-axis. A pair of Y-axis steering coils 20A and 20B are positioned at the twelve o'clock and six o'clock positions, respectively, and a pair of X-axis steering coils 21A and 21B are positioned at the three o'clock and nine o'clock positions, respectively. Each steering coil is a small electromagnet driven by power supplied from the host unit over the connecting cable. It is also feasible to have an on-board battery-based supply for powering the probe. Each steering coil produces a field having a direction substantially perpendicular to vector 19 of the main field. Only vector 22 of steering coil 20A is shown for purposes of clarity. The polarity of the steering fields in each pair is reversible, but their field vectors always point in the same direction.

The steering coils function in a manner similar to the electron-beam deflector yokes in a cathode-ray tube (CRT). The deflector yokes in a CRT move or scan an electron beam alternately left and right at a high rate, while gradually deflecting it up and down at a much lower rate to produce a rectangular scanning pattern on a screen to produce an image. Likewise, steering coil pairs 20 and 21 rapidly steer vector 19 of the main field in a similar pattern.

Figure 4B:
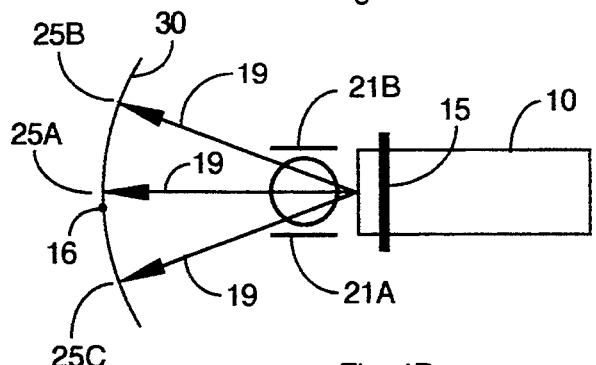
FIG. 4B is a plan view of the magnet and steering coils of FIG. 4A.

Plan view FIG. 4B shows one horizontal scanning cycle. Imaging point 16 is swept along an arc 30 as vector 19 is steered from one side to the other. An arc is described because point 16 will always be the same distance from magnet 10, whether at intermediate position 25A, or at extreme positions 25B and 25C at the ends of the scan. Point 16 is shown at an arbitrary position on arc 30 in FIG. 4B.

Point 16 will also describe a vertical arc as it is being steered up and down (not shown). In three-dimensions, point 16 will describe a curved imaging surface 23 which is concave toward magnet 10, as also shown in FIG. 4A. During each horizontal scanning cycle, coil 15 alternately produces a burst and detects the echo to image many points of interest. These are combined to produce an internal image of sample 13 in the form of a concave arcuate slice.

When combination coil 15 is energized, its field strength is added to that of the main field. As a result, imaging point 16, and consequently imaging surface 23 may be moved along the Z-axis toward and away from magnet 10. The field strength of combination coil 15 can be modulated to move imaging surface 23 slightly after each vertical scanning cycle, and the high frequency burst required for the burst cycle may be superimposed on the base current that positions the imaging point. Gradually moving imaging surface 23 creates a stack of imaging surfaces, as shown in FIG., 4C. Integration of these sectional images produces a three-dimensional image of the interior of the sample. The MRI probe according to this embodiment of the invention can image up to a few centimeters from the probe, Instead of curved image slices, flat slices can be produced by altering the scanning of point 16 so that instead of curved imaging surface 23, a flat imaging plane 26 is described, as shown in the top view in FIG. 5. This is achieved by modulating the field strength of combination coil 15 as vector 19 is deflected. When vector 19 is at intermediate position 27A, its strength is the same as at position 25A in FIG. 4B. As vector 19 is steered horizontally away from intermediate position 25A, the field strength of combination coil 15 is increased gradually, so that point 16 is moved to describe a straight line between extreme positions 27B and 27C. When vector 19 is steered vertically (not shown), the field strength of combination coil 15 is also similarly modulated, so that in 3-dimensions, the movement of point 16 will describe a flat imaging plane 26. As a result, a flat image slice will be taken of whatever sample is penetrated by plane 26. Image plane 26 can be moved along the Z-axis as described in conjunction with FIG. 4C to produce a 3-dimensional image having a volume of several cubic centimeters.

Figure 4C:
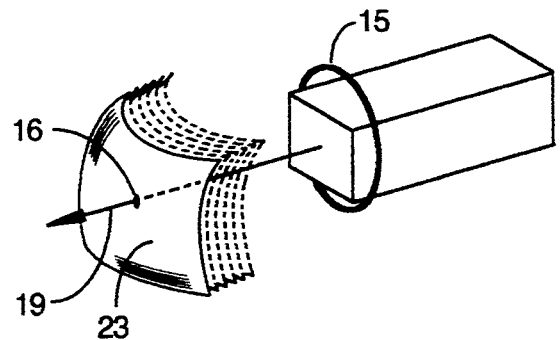
FIG. 4C is an isometric view of the magnet and coils of FIG. 4A showing shift of a curved imaging surface.
Figure 5:
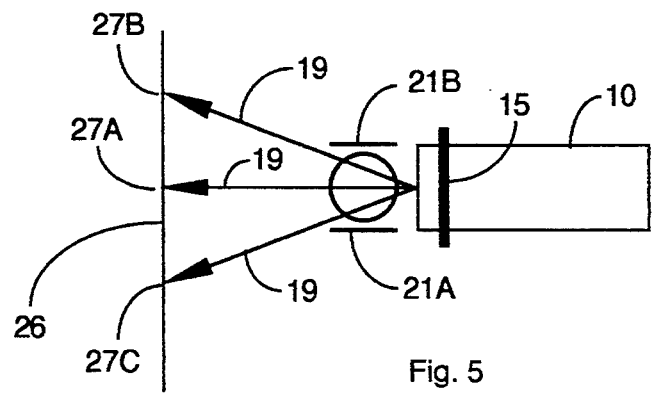
FIG. 5 is a plan view of the magnet of FIG. 4A showing the steering coils and a substantially flat imaging surface.

A flat image slice can also be produced using data acquired with the scanning technique shown in FIGS. 4A to 4C, This is done by producing a 3-dimensional image as a result of sequential curved slices, and storing it as a three-dimensional bit map in the computer memory. The data points lying in a desired plane are then selected and displayed to compose a flat image.

Figure 6:
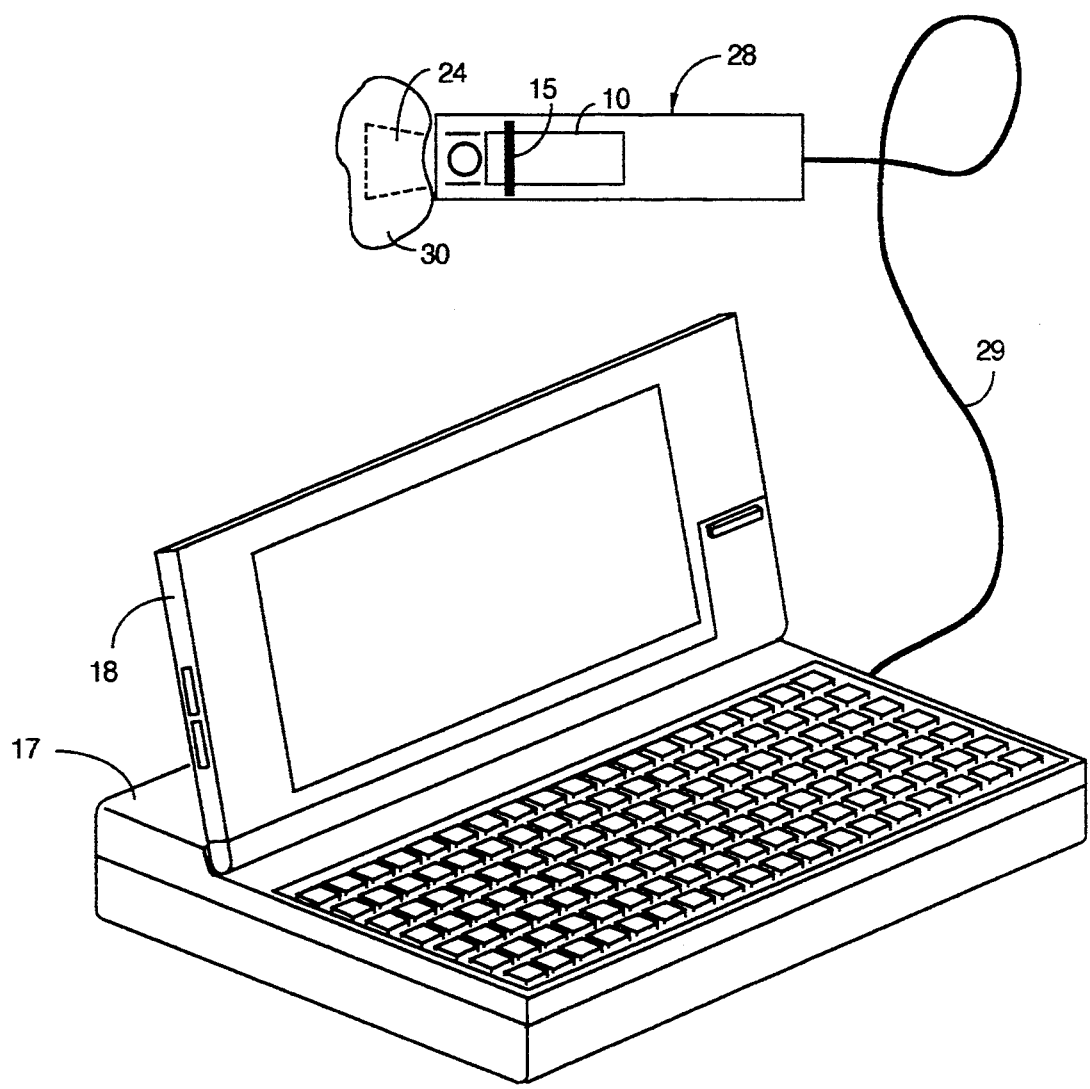
FIG. 6 is a partly diagrammatical illustration of a hand-held MRI probe according to an embodiment of the invention, connected to a general-purpose computer, and adjacent to a tissue sample to be scanned.

The small size of magnet 10, combination coil 15, and steering coil pairs 20 and 21 allow for packaging in such as a small tubular housing to provide a hand-held probe 28, as shown in FIG. 6. The probe is connected by a flexible cable 29 to a host, such as notebook computer 17 in one embodiment, so the entire MRI system that results is highly portable. Imaging volume 24 can be projected up to a few centimeters beneath the surface of a sample. The resulting hand-held probe and its ability to image provides a valuable tool for many purposes. For example, a heart surgeon involved in a bypass procedure, after the heart is exposed and the area of interest is located, may image the artery to be bypassed at the point of surgery, providing extremely valuable information as surgery proceeds. As another example, an eye surgeon may look at the inner structure of the eye in performing delicate surgical procedures, and may image foreign matter in accidents involving eye tissue.

The magnetic fields produced by combination coil 15 and steering coils 20 and 21 will gradually degrade permanent magnet 10. In another aspect of the invention, a calibration device 31 shown in FIG. 7A is used to compensate for the deterioration. Device 31 includes a receptacle 32 into which probe 28 is inserted. A reference object 33 in the form of two straight, water-filled tubes 34A and 34B are arranged in a cross, and positioned directly in front of probe 28.

Figure 7B:
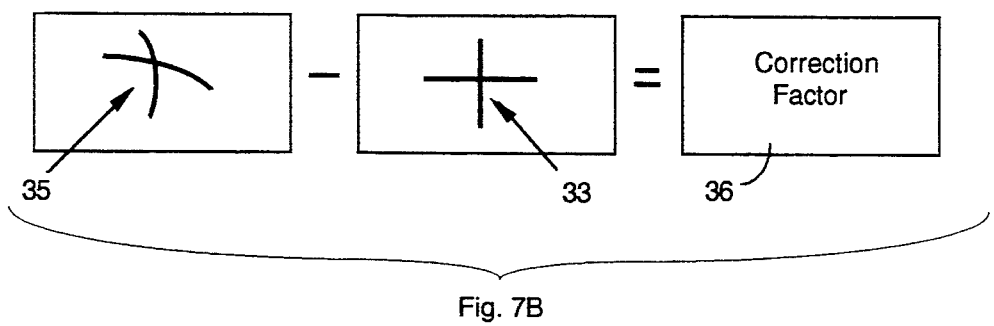
FIG. 7B is a diagram of calibration images for developing correction factors.
Figure 7A:
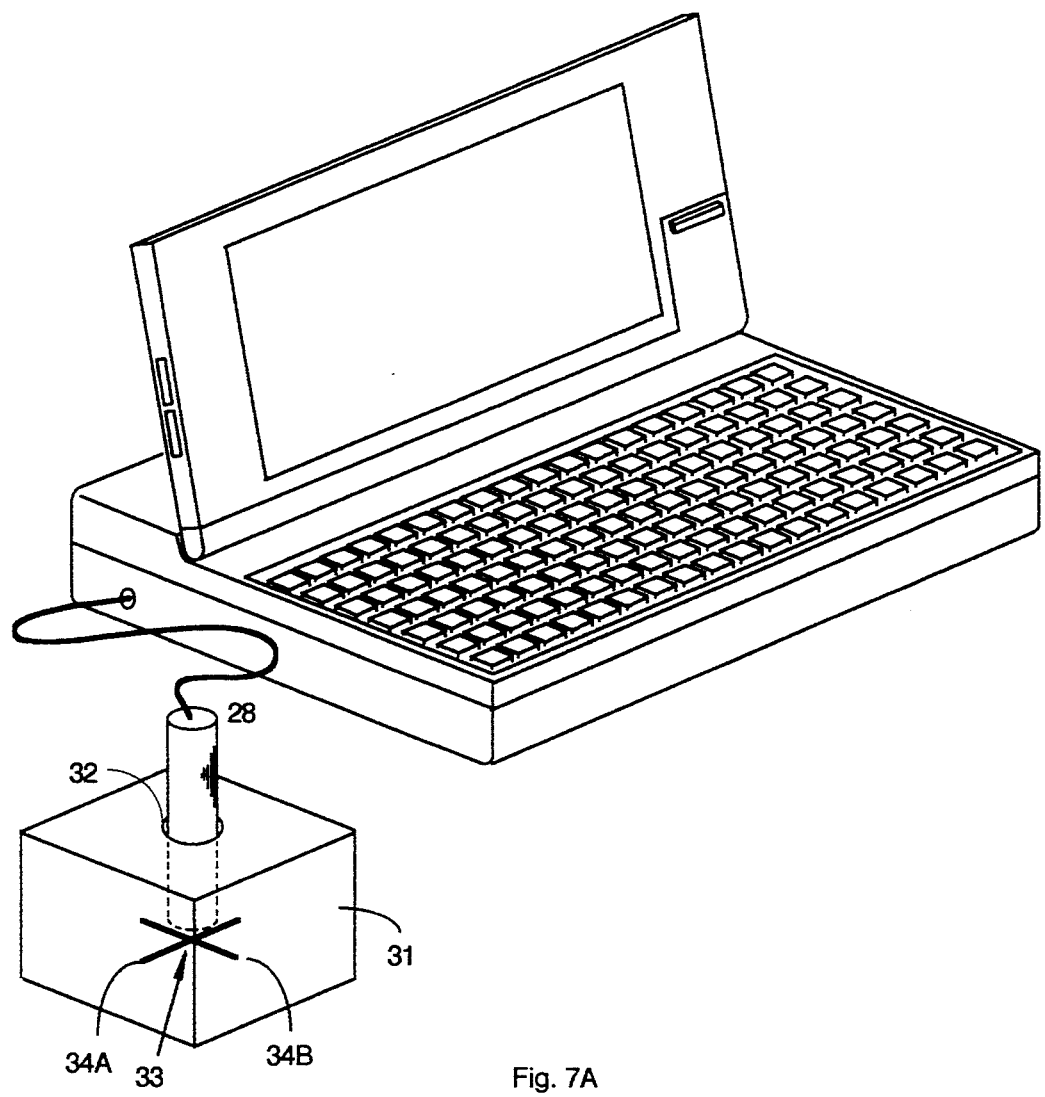
FIG. 7A is an illustration of a calibration device for use with the hand-held probe of the present invention, together with a probe and a connected computer.

FIG. 7B shows a distorted image 35 of reference object 33. Distortion will be by an amount proportional to the degradation of magnet 10. Also in FIG. 7B an idealized image 37 of the reference cross is shown. This image may be stored based on empirical knowledge of the reference, and is the image that would be made if there were no deterioration in the permanent magnet.

Suitable software takes the difference, point-by-point, between reference image 37 and the distorted shape and dimensions of image 35 to produce a table of calibration factors 36, stored in memory in computer 17. Subsequent images of any objects taken by probe 28 may then be corrected by factors 36, so that accurate images may be displayed. The frequency of calibrations depends on the rapidity of magnet degradation. Maximum imaging accuracy can be maintained by calibrating probe 28 after each use. There is a point, to be determined empirically, beyond which a magnet should be replaced.

The hand-held MRI probe according to embodiments of the invention is extremely compact and portable, It can be used by paramedics in the field to diagnose injuries such as skull fractures and broken ribs. Unlike a conventional MRI machine, which requires patients to lie down within the machine and to be stripped of ferrous objects such as belt buckles, the portable MRI probe can be used without imposing such inconvenient requirements on the patients. The MRI probe of the present invention can be easily set up in a doctor's office, so that MRI imaging will become more easily available to patients, who will no longer have to visit major medical facilities where conventional MRI machines are installed and operable.

Although the above descriptions are specific, they should not be construed as limitations on the scope of the invention, but only as preferred embodiments of the invention. Many other variations are possible. For example, other types of magnets can be used. Instead of being rectangular, the magnet can be cylindrical, or any other suitable shape. The hand-held MRI probe can be used to image other objects other than human bodies, The combination burst and sensor coil can be replaced by separate coils. Other ways of moving the imaging point along the three axes can be used. Reference objects in other shapes and sizes can be used to calibrate the probe, Accordingly, the scope of the invention should be not be determined solely by the embodiments illustrated, but by the appended claims.

What is claimed is:

1. A hand-held probe for magnetic resonance imaging comprising;
   an elongated housing having a first end and a second end and configured to be held and manipulated in a user's hand;
   a permanent magnet supported within the housing with one pole facing the first end of the housing, a pole axis of the permanent magnet substantially parallel with the length of the elongated housing; and
   an electromagnetic combination burst and detector coil supported by the housing and positioned with an axis of the burst and detector coil coaxial with the pole axis of the permanent magnet.

2. A hand-held probe as in claim 1 wherein the permanent magnet is a rare earth magnet.

3. A hand-held probe as in claim 2 wherein the permanent magnet is a rare earth magnet comprising neodymium-iron-boron magnet material.

4. A hand-held probe as in claim 1 further comprising a variable magnetic deflector apparatus supported by the housing and positioned between the permanent magnet and the first end to deflect the magnetic field of the permanent magnet.

5. A hand-held probe as in claim 4 wherein the variable magnetic deflector apparatus comprises a first pair of coaxial electromagnetic steering coils positioned with a common axis of the first pair of electromagnetic steering coils substantially orthogonal to the pole axis of the permanent magnet, and a second pair of coaxial electromagnetic steering coils positioned with a common axis of the second pair of electromagnetic steering coils substantially orthogonal to the pole axis of the permanent magnet and of the common axis of the first pair of magnetic steering coils.

6. A magnetic resonance imaging system comprising:
   a general-purpose computer system; and
   a hand held probe having an elongated enclosure housing a permanent magnet with one pole facing a first end of the enclosure and a pole axis of the permanent magnet substantially parallel with the length of the enclosure, and an electromagnetic burst and sensor coil positioned with an axis of the coil coaxial with the pole axis of the permanent magnet;
   means associated with the general-purpose computer system for driving the burst and detector coil to resonate atomic elements in atoms a sample adjacent the first end, and to detect signals on the burst and detector coil induced by the resonating atomic elements.

7. A magnetic resonance imaging system as in claim 6 further comprising a variable magnetic deflector apparatus supported by the housing and positioned between the permanent magnet and the first end to deflect the magnetic field of the permanent magnet.

8. A magnetic resonance imaging system as in claim 7 wherein the magnetic deflector apparatus comprises two pairs of coaxial electromagnetic steering coils controllable from the general-purpose computer and positioned with steering coil axes at substantially right angles to one another and to the pole axis of the permanent magnet.

9. A magnetic resonance imaging system as in claim 6 wherein the permanent magnet in the hand-held probe comprises a rare-earth magnet material.

10. A magnetic resonance imaging system as in claim 9 wherein the rare earth material is neodymium-iron-boron.

11. A magnetic resonance imaging system as in claim 6 further comprising a calibration apparatus comprising a known imagable shape and a register for the hand-held probe in the calibration apparatus to sense the known shape, and the general-purpose computer compares a real-time image of the known imagable shape with an idealized image to provide a table of correction values for correcting images for deterioration of the strength of the permanent magnet.

12. A method for magnetic resonance imaging of small sample volumes, comprising steps of:
   (a) placing a first end of an elongated enclosure housing a permanent magnet with one pole facing the first end of the enclosure and a pole axis of the permanent magnet substantially parallel with the length of the enclosure, proximate a surface of a sample volume to be imaged;
   (b) providing a high frequency burst field with an electromagnetic coil positioned to provide a magnetic field coaxial with that provided by the permanent magnet, at a first frequency to excite specific nuclei in the sample located at points in the sample with a first specific magnetic field strength, such points describing a first arcuate surface within the sample;
   (c) suspending the high frequency burst and sensing magnetic response produced by the excited nuclei with the electromagnetic coil;
   (d) recording the sensed magnetic response produced by excited nuclei located in the first arcuate surface; and
   (e) repeating steps (b), (c), and (d) with different burst frequencies to test the sample at positions within the sample where the magnetic field strength differs from the magnetic field strength at the first arcuate surface.

13. The method of claim 12 comprising a further step of computing and displaying an image on a display screen based on the presence and absence of magnetic response produced by excited nuclei in the sample volume.

14. A method for magnetic resonance imaging of small sample volumes, comprising steps of:
   (a) placing a first end of an elongated enclosure housing a permanent magnet with one pole facing the first end of the enclosure and a pole axis of the permanent magnet substantially parallel with the length of the enclosure, proximate a surface of a sample volume to be imaged;
   (b) providing a biasing magnetic field with an electromagnetic coil positioned to provide the biasing field coaxial with that provided by the permanent magnet, providing a summed magnetic field being the sum of the fields provided by the permanent magnetic and the electromagnetic coil;
   (c) providing a high frequency burst field with the electromagnetic coil at a frequency to excite specific nuclei in the sample located at a sensing point;
   (d) suspending the high frequency burst and sensing magnetic response from excited nuclei at the sensing point with the electromagnetic coil;
   (e) recording the presence or absence of the specific nuclei at the sensed point in the sample;
   (f) deflecting the summed magnetic field of the permanent magnet and the biasing field with a magnetic deflection apparatus to move the sensing point to a new location in the sample; and (g) repeating steps (c), (d), (e) and (f) with a common burst frequency to test the sample at an array of sensing points within the sample by deflecting the summed field with the deflection apparatus, the array of sensing points representing a two-dimensional slice through the sample.

15. The method of claim 14 comprising a further step (h) of computing and displaying an image on a display screen based on the presence and absence of the specific nuclei at sensed points in the two-dimensional slice through the sample volume.

16. The method of claim 14 further comprising returning to step (b) after step (h), incrementing the bias field, and repeating steps (c)–(h) to develop an image map of a second slice.

17. The method of claim 16 wherein the steps are repeated to provide a three-dimensional image map of the sample comprising multiple slices,

* * * * *